(12) United States Patent
Sato et al.

(10) Patent No.: US 10,999,538 B2
(45) Date of Patent: May 4, 2021

(54) IMAGING UNIT

(71) Applicant: FUJIKURA LTD., Tokyo (JP)

(72) Inventors: Takao Sato, Sakura (JP); Hideo Shiratani, Sakura (JP); Wataru Oishi, Sakura (JP)

(73) Assignee: Fujikura Ltd., Tokyo (JP)

(*) Notice: Subject to any disclaimer, the term of this patent is extended or adjusted under 35 U.S.C. 154(b) by 266 days.

(21) Appl. No.: 16/370,288

(22) Filed: Mar. 29, 2019

(65) Prior Publication Data

US 2019/0313037 A1 Oct. 10, 2019

(30) Foreign Application Priority Data

Apr. 4, 2018 (JP) .............................. JP2018-072588

(51) Int. Cl.
| | | |
|---|---|---|
| *A61B 1/00* | (2006.01) | |
| *H04N 5/335* | (2011.01) | |
| *H04N 5/225* | (2006.01) | |
| *H01L 27/146* | (2006.01) | |
| *A61B 1/05* | (2006.01) | |

(52) U.S. Cl.
CPC ........... *H04N 5/335* (2013.01); *A61B 1/0011* (2013.01); *A61B 1/00114* (2013.01); *A61B 1/051* (2013.01); *H01L 27/14601* (2013.01); *H04N 5/225* (2013.01); *H04N 5/2253* (2013.01); *H04N 5/2257* (2013.01); *H04N 2005/2255* (2013.01)

(58) Field of Classification Search
CPC ...... H04N 5/335; H04N 5/2253; H04N 5/225; H04N 5/2257; H04N 2005/2255; H01L 27/14601; A61B 1/051; A61B 1/00114; A61B 1/0011
See application file for complete search history.

(56) References Cited

U.S. PATENT DOCUMENTS

| | | | |
|---|---|---|---|
| 2018/0006388 A1* | 1/2018 | Yamada | ................. H01R 12/59 |
| 2018/0070803 A1* | 3/2018 | Mikami | ............ A61B 1/00163 |
| 2018/0132704 A1* | 5/2018 | Yamada | ............ A61B 1/00128 |
| 2019/0216304 A1* | 7/2019 | Kimura | .............. G02B 23/2484 |

FOREIGN PATENT DOCUMENTS

| | | |
|---|---|---|
| JP | H04-035474 A | 2/1992 |
| JP | H09061731 A | 3/1997 |
| JP | H11-019035 A | 1/1999 |

(Continued)

*Primary Examiner* — Mekonnen D Dagnew
(74) *Attorney, Agent, or Firm* — Osha Bergman Watanabe & Burton LLP

(57) ABSTRACT

An imaging unit includes: a solid-state imager including an imaging surface disposed on a front surface of the solid-state imager and electrode pads disposed separately from each other on a rear surface of the solid-state imager that is opposite to the front surface; and a coaxial cable electrically connected to the electrode pads on the rear surface of the solid-state imager. The coaxial cable includes: an inner coated wire including an internal conductor that includes a plurality of element wires and an inner insulating layer that coats a surrounding circumference of the internal conductor; an external conductor including a plurality of element wires that surround the inner coated wire; and an outer insulating layer that coats the external conductor.

6 Claims, 6 Drawing Sheets

(56) References Cited

FOREIGN PATENT DOCUMENTS

| | | |
|---|---|---|
| JP | 2000125161 A | 4/2000 |
| JP | 2001178675 A | 7/2001 |
| JP | 2003210463 A | 7/2003 |
| JP | 2006109097 A | 4/2006 |
| JP | 2010068930 A | 4/2010 |
| JP | 2011050496 A | 3/2011 |
| JP | 2014042810 A | 3/2014 |
| JP | 2015144102 A | 8/2015 |
| JP | 2017-018415 A | 1/2017 |
| JP | 2017046854 A | 3/2017 |
| JP | 2017195965 A | 11/2017 |
| JP | 2018038677 A | 3/2018 |
| WO | 2015045467 A1 | 4/2015 |

* cited by examiner

IMAGING UNIT

CROSS REFERENCE TO RELATED APPLICATIONS

This application claims priority from Japanese Patent Application No. 2018-072588, filed in Japan on Apr. 4, 2018, the contents of which are incorporated herein by reference in their entirety.

TECHNICAL FIELD

The present invention relates to an imaging unit including a solid-state image sensing device such as a complementary metal oxide semiconductor (so-called CMOS) or a charge coupled device (so-called CCD) that can be used for an electronic endoscope or the like.

BACKGROUND

In an electronic endoscope, a configuration in which an imaging unit configured to electrically connect a solid-state image sensing device (hereinafter, also simply referred to as an imaging device) to a distal end of an electric wire via a wiring substrate is housed in a flexible tube made of a resin is widely employed (for example, Japanese Unexamined Patent Publication, First Publication No. 2017-18415, hereinbelow, referred to as Patent Document 1).

In this type of imaging unit, distal ends of electric wires are electrically connected to a plurality of wirings of the wiring substrate, and the respective electric wires are electrically connected to the imaging device via the wirings of the wiring substrate.

The wiring substrate is disposed on a rear side of the imaging device by electrically connecting the wirings to electrodes on a rear surface of the imaging device opposite to an imaging surface at a front end thereof.

In imaging units used for endoscopes or the like, as a countermeasure against noise, use of coaxial cables for electric wires has become common in recent years.

When a coaxial cable is used, a wiring substrate (coaxial cable wiring substrate) including an electrode pad (internal conductor connecting pad) to which a distal end portion of an internal conductor of the coaxial cable is soldered, and an electrode pad (external conductor connecting pad) to which a distal end portion of an external conductor of the coaxial cable is soldered is used. The coaxial cable wiring substrate includes a wiring for electrically connecting the internal conductor connecting pad to the imaging device and a wiring for electrically connecting the external conductor connecting pad to the imaging device.

As a coaxial cable wiring substrate, there are one using a rigid substrate and one using a flexible printed wiring substrate (hereinafter also referred to as an FPC). The coaxial cable wiring substrate includes a connection front end portion connected to the imaging device by soldering the wiring to the electrode on the rear surface of the imaging device and a rear side extended portion extending toward the imaging device rear side from the connection front end portion. The rear side extended portion of the coaxial cable wiring substrate is generally in a flat plate shape or strip shape having a pair of the internal conductor connecting pad and the external conductor connecting pad on one side or both sides. The internal conductor connecting pad and the external conductor connecting pad are provided separately from each other in an extending direction (front-rear direction) of the rear side extended portion.

An imaging unit has a rigid portion that does not easily bend at a front end portion at which an imaging device is positioned.

For example, an imaging unit in which a rigid coaxial cable wiring substrate is used may include a rigid portion constituted by an imaging device, a lens unit fixed to a front end surface of the imaging device, a coaxial cable wiring substrate provided on a rear side of the imaging device, and soldered portions in which respective distal end portions of an internal conductor and an external conductor of a coaxial cable are soldered to electrode pads of the coaxial cable wiring substrate.

The soldered portions include solder that has soldered the respective distal end portions of the internal conductor and the external conductor of the coaxial cable to the electrode pads of the coaxial cable wiring substrate.

A rear side extended portion of a coaxial cable wiring substrate in a conventional structure using an FPC (hereinafter referred to as a coaxial cable FPC) has a certain level of flexibility before an internal conductor and an external conductor of the coaxial cable are soldered. However, in the rear side extended portion of the coaxial cable FPC, in a state in which the internal conductor and the external conductor of the coaxial cable are respectively soldered to an internal conductor connecting pad and an external conductor connecting pad, an entire region in which the coaxial cable is provided substantially becomes a portion of a rigid portion due to rigidity of the coaxial cable provided along the rear side extended portion and rigidity of soldered portions of the internal conductor and the external conductor.

The imaging unit of the conventional structure assembled using the coaxial cable FPC includes a rigid portion constituted by an imaging device, a lens unit, a coaxial cable wiring substrate, and soldered portions in which the internal conductor and the external conductor of the coaxial cable are soldered with respect to electrode pads of the rear side extended portion of the coaxial cable wiring substrate.

In an imaging unit used for endoscopes or the like, when a length of the rigid portion of the front end portion at which the imaging device is positioned (a dimension in a front-rear direction of the imaging device, hereinafter also referred to as a rigid portion length) is long, in a case in which a swinging operation for changing an orientation of the front end portion of the imaging unit at which the imaging device is positioned is performed in a narrow conduit or the like, a case in which a movable range of the front end portion of the imaging unit due to a swinging operation cannot be sufficiently secured is likely to occur. Therefore, a length of the rigid portion of the front end portion (a dimension in a front-rear direction of the imaging device, hereinafter also referred to as a rigid portion length) is required to be reduced in the imaging unit.

In view showing this requirement, in the conventional coaxial cable wiring substrate, reducing an extended length of the rear side extended portion from the connection front end portion is being investigated. However, in the conventional coaxial cable wiring substrate, in order to prevent short-circuiting between the soldered portions of the internal conductor and the external conductor of the coaxial cable, it is necessary to secure a separation distance in an extending direction (front-rear direction) of the rear side extended portion between the internal conductor connecting pad and the external conductor connecting pad. Therefore, in the conventional imaging unit, it has been difficult to reduce an extension dimension of the rear side extended portion of the coaxial cable wiring substrate and reduce the rigid portion length.

SUMMARY

The invention provides an imaging unit that can easily realize reduction of a rigid portion length.

One or more embodiments of the invention provide one or more of the following aspects.

An imaging unit according to one or more embodiments includes a solid-state image sensing device, and a coaxial cable electrically connected to an electrode pad on a rear surface opposite to a front surface on which an imaging surface of the solid-state image sensing device is positioned, in which the coaxial cable includes an inner coated wire in which a surrounding circumference of an internal conductor made of a plurality of element wires is coated with an inner insulating layer, an external conductor made of a plurality of element wires provided to surround the inner coated wire and an outer insulating layer coating the external conductor, an external conductor aggregate-wire portion in which a plurality of element-wires of the external conductor are aggregated from a front end of the outer insulating layer and the inner coated wire extend in directions different from each other, and an internal conductor front side extended portion extending from a front end of the inner insulating layer of the inner coated wire extending from the front end of the outer insulating layer and the external conductor aggregate-wire portion are connected to the electrode pads provided separately from each other on the rear surface of the solid-state image sensing device.

Respective extended lengths of the internal conductor and the external conductor aggregate-wire portion from the front end of the outer insulating layer to the electrode pads of the solid-state image sensing device may be aligned to be the same as each other.

The imaging unit may include a protective resin portion formed by implanting the inner coated wire and the external conductor aggregate-wire portion into a rear side of the solid-state image sensing device and avoiding implant of the outer insulating layer thereinto.

The imaging unit may further include a resin sleeve in which the protective resin portion is housed, and the protective resin portion may be formed in the entire region on the solid-state image sensing device side from the front end of the outer insulating layer inside the resin sleeve.

Any one or both of the internal conductor front side extended portion and the external conductor aggregate-wire portion may be a twisted aggregate-wire in which a plurality of element wires are twisted together.

Any one or both of the internal conductor front side extended portion and the external conductor aggregate-wire portion may be configured by integrating a plurality of element wires by soldering.

According to the imaging unit according to one or more embodiments of the invention, since the use of coaxial cable wiring substrate can be omitted due to the configuration in which the respective ends of the internal conductor front side extended portion and the external conductor aggregate-wire portion of the coaxial cable are directly soldered to the electrode pads of the imaging unit, reduction of the rigid portion length can be easily realized. The imaging unit according to one or more embodiments of the invention is advantageous in that a movable range of the imaging device in a swinging operation is stably secured to a sufficient magnitude.

DETAILED DESCRIPTION

Hereinafter, an imaging unit according to embodiments of the invention will be described with reference to the drawings.

First, an imaging unit according to one or more embodiments of the invention will be described.

Figure 1:
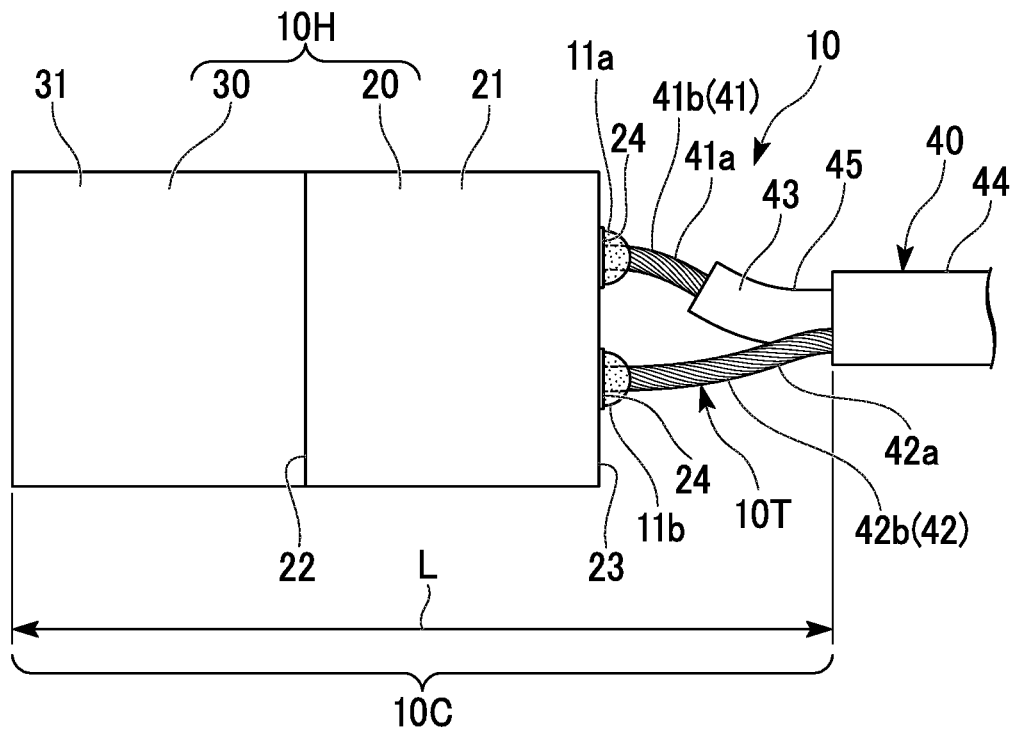
FIG. 1 is a front view showing a structure in the portion near an imaging head of an imaging unit according to one or more embodiments of the invention.
Figure 2:
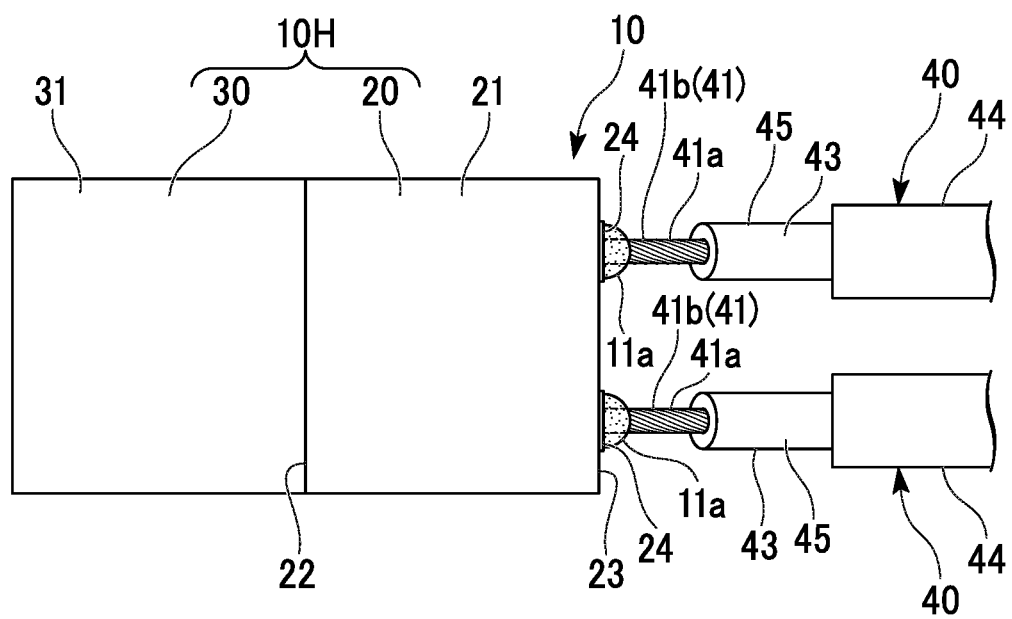
FIG. 2 is a plan view showing a structure in the portion near the imaging head of the imaging unit of FIG. 1 according to one or more embodiments.

FIGS. 1 and 2 show an imaging unit 10 according to one or more embodiments.

Figure 3:
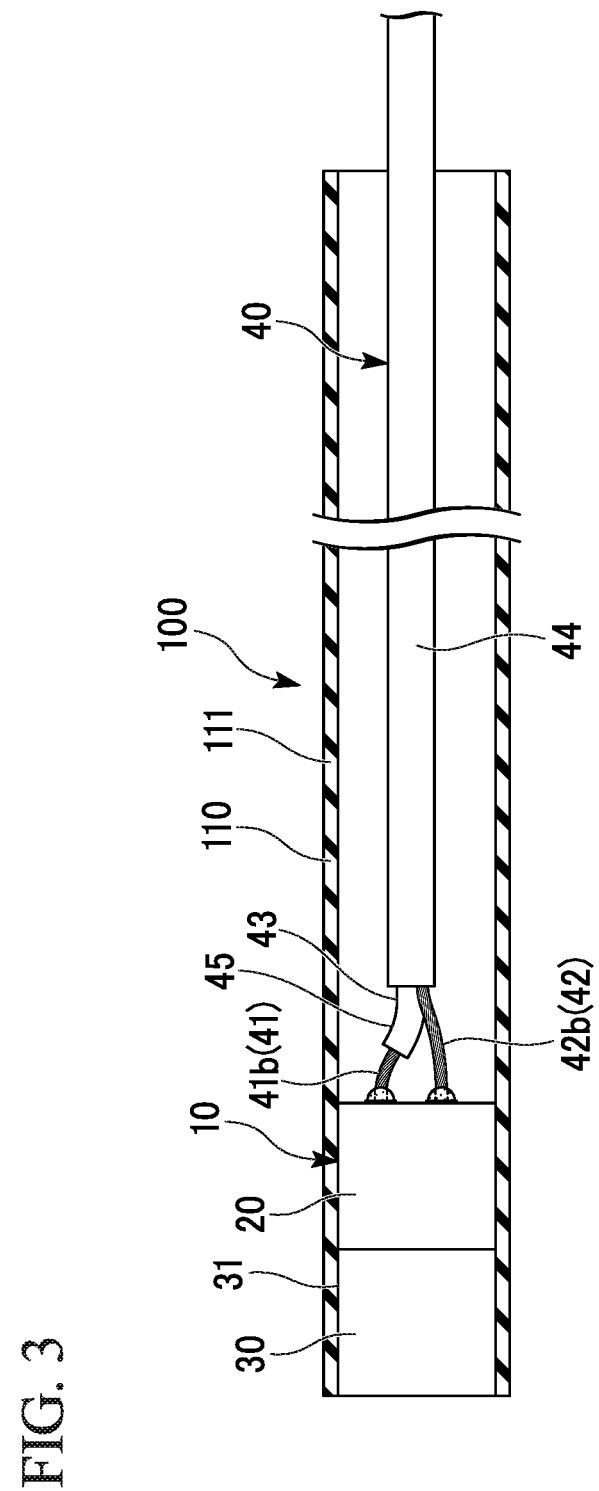
FIG. 3 is a front cross-sectional view showing an example of an imaging module having a configuration in which the imaging unit of FIG. 1 is housed in a protective tube according to one or more embodiments.

FIG. 3 shows an example of an imaging module 100 in which the imaging unit 10 is housed and assembled in a protective tube 110 according to one or more embodiments. The imaging unit 10 can be used in assembly of the imaging module 100.

The imaging unit 10 shown in FIGS. 1 and 2 includes a solid-state image sensing device 20 (hereinafter also simply referred to as an imaging device or solid-state imager), a lens unit 30 fixed to a front surface 22 of the imaging device 20 (specifically, a front surface of a device main body 21), and an electric cable 40 electrically connected to the imaging device 20.

A complementary metal oxide semiconductor (a so-called CMOS), a charge coupled device (a so-called CCD), or the like is used for the imaging device 20.

The imaging device 20 includes a device main body 21 having a rear surface 23 parallel to the front surface 22 and formed on a side opposite to the front surface 22, and an electrode pad 24 formed on the rear surface 23 of the device main body 21.

The device main body 21 shown in FIGS. 1 and 2 is a member formed in a rectangular parallelepiped shape (specifically, a rectangular plate shape). However, a specific shape of the device main body 21 is not restricted to a rectangular parallelepiped shape, but may be any shape as long as the front surface 22 and the rear surface 23 parallel to the front surface 22 are formed, and may be, for example, a columnar shape or the like.

The imaging unit 10 will be described on the assumption that the lens unit 30 side is a front side and a side opposite to the lens unit 30 side is a rear side.

The imaging unit 10 includes an imaging head 10H constituted by the imaging device 20 and the lens unit 30. A front-rear direction of the imaging device 20 (a distance direction between the front surface 22 and the rear surface 23) is a front-rear direction in the imaging head 10H.

The lens unit 30 has a configuration in which a lens is housed in a cylindrical lens housing 31. The lens unit 30 is aligned such that the lens in the lens housing 31 is positioned on a light receiving optical axis of an imaging surface at a center portion of the front surface 22 of the imaging device 20 and fixed to the front surface 22 of the imaging device 20.

The imaging device 20 receives light incident on the imaging surface from the front side of the lens unit 30 via an inner region of the lens housing 31 to capture an image.

Specifically, the electric cable 40 is a coaxial cable having an internal conductor 41 and an external conductor 42. Hereinafter, the electric cable 40 is also referred to as a coaxial cable.

Figure 7:
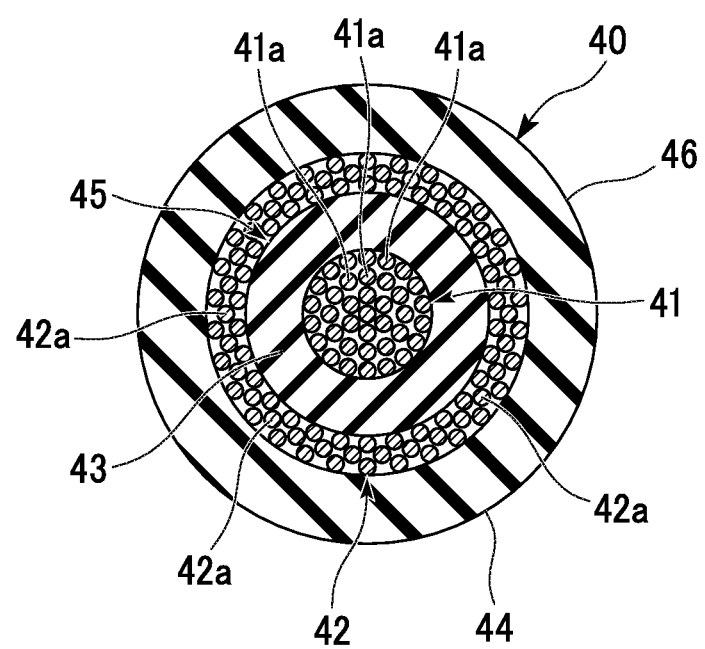
FIG. 7 is a cross-sectional view showing a cross-sectional structure perpendicular to a longitudinal direction of a cable main body, which is a portion in which an outer insulating layer is present in a coaxial cable of the imaging unit of FIG. 1, according to one or more embodiments.

As shown in FIG. 7, in accordance with one or more embodiments, the coaxial cable 40 includes the internal conductor 41, an inner insulating layer 43 coating a surrounding circumference of the internal conductor 41, the external conductor 42 provided to coat a surrounding circumference of the inner insulating layer 43, and an outer insulating layer 44 coating the external conductor 42. The coaxial cable 40 includes an inner coated wire 45 constituted by the internal conductor 41 and the inner insulating layer 43 coating the surrounding circumference of the internal conductor 41.

The internal conductor 41 and the external conductor 42 are each constituted by a plurality of element wires made of a metal.

The internal conductor 41 is formed by twisting a plurality of element wires 41a together.

The external conductor 42 is formed with a plurality of element wires 42a (hereinafter also referred to as external conductor element wires) spirally provided between the inner insulating layer 43 and the outer insulating layer 44 inside the outer insulating layer 44. The plurality of external conductor element wires 42a are provided to surround the inner coated wire 45.

The inner insulating layer 43 and the outer insulating layer 44 are an electrically insulating resin coating material (resin coating).

As shown in FIGS. 1 and 2, at a front end portion of the coaxial cable 40, there are an aggregate-wire portion 42b (hereinafter also referred to as an external conductor aggregate-wire portion) in which a plurality of portions (front side extended portions) of the external conductor element wires 42a extending from a front end of the outer insulating layer 44 are aggregated and formed into a linear shape, and a front side extended portion 41b (hereinafter also referred to as an internal conductor front side extended portion) which is a portion of the internal conductor 41 extending from a front end of the inner insulating layer 43.

Further, FIG. 7 shows a cross-sectional structure perpendicular to a longitudinal direction of a cable main body 46 (hereinafter also referred to as a coaxial cable main body) which is a portion in which the outer insulating layer 44 of the coaxial cable 40 is present.

At the front end portion of the coaxial cable 40, the inner coated wire 45 has a portion (a front side protruding portion) protruding from the front end of the outer insulating layer 44. A portion 43a (a front side extended portion) of the inner insulating layer 43 positioned at the front side protruding portion of the inner coated wire 45 will also be referred to as an inner insulating layer front side extended portion hereinafter.

An internal conductor front side extended portion 41b extends from a front end of the inner insulating layer front side extended portion 43a positioned in the inner coated wire 45.

The internal conductor front side extended portion 41b is a portion of the internal conductor 41 which is a twisted wire.

An external conductor aggregate-wire portion 42b is one (aggregate-wire) in which front side extended portions of a plurality of external conductor element wires 42a are aggregated and collectively combined.

Specifically, the external conductor aggregate-wire portion 42b shown in FIG. 1 is formed as a twisted wire (twisted aggregate-wire) in which aggregates of the front side extended portions of the plurality of external conductor element wires 42a are twisted. However, the external conductor aggregate-wire portion 42b may be formed in a linear shape (untwisted aggregate-wire) in which the front side extended portions of the plurality of external conductor element wires 42a are aggregated while maintaining a state in which they are substantially parallel to each other without being twisted.

In the present specification, descriptions where neither a twisted aggregate-wire nor an untwisted aggregate-wire is specified with respect to the external conductor aggregate-wire portion apply to both the external conductor aggregate-wire portion of the twisted aggregate-wire and the external conductor aggregate-wire portion of the untwisted aggregate-wire.

The external conductor aggregate-wire portion 42b is formed using the front side extended portions of all or some of the element wires 42a constituting the external conductor 42.

Among the external conductor element wires 42a, the external conductor element wires 42a not used for forming the external conductor aggregate-wire portion 42b are those having no front side extended portion or those having a very small front side extended portion (a length of the front side extended portion is 200 μm or less).

A plurality of electrode pads 24 (four in FIGS. 1 and 2) are provided on the rear surface 23 of the device main body 21 of the imaging device 20 (hereinafter also referred to as a device main body rear surface).

The plurality of electrode pads 24 are provided separately from each other.

As shown in FIG. 1, respective distal ends (front ends) of the internal conductor front side extended portion 41b and the external conductor aggregate-wire portion 42b of the coaxial cable 40 are electrically connected to the imaging device 20 by soldering them to the electrode pads 24 different from each other on the rear surface 23 of the device main body 21 of the imaging device 20 (hereinafter also referred to as a device main body rear surface).

The coaxial cable 40 is attached to the imaging device 20 by soldering the respective distal ends of the internal conductor front side extended portion 41b and the external conductor aggregate-wire portion 42b to the electrode pads 24 of the imaging device 20. The coaxial cable 40 is provided on the rear side of the imaging device 20.

Specifically, the imaging unit 10 shown in FIGS. 1 and 2 is configured by electrically connecting the internal conductor front side extended portion 41b and the external conductor aggregate-wire portion 42b of two coaxial cables 40 to the imaging device 20.

For example, when only a single-wire cable is used instead of the coaxial cable 40 for the imaging unit 10 shown in FIGS. 1 and 2, the same number of single-wire cables as the total number (four in FIGS. 1 and 2) of the internal conductor front side extended portion 41b and the external conductor aggregate-wire portion 42b of all the coaxial cables 40 of the imaging unit 10 shown in FIGS. 1 and 2 extend from the imaging device 20 toward the rear side.

Since a dead space generated between the cables brought into contact with each other can be made small, a case in which the plurality of coaxial cables 40 are aggregated is advantageous in terms of reducing a cross-sectional dimension (thickness) perpendicular to the longitudinal direction and securing good flexibility compared to a case in which twice as many single-wire cables as coaxial cables 40 are aggregated.

As shown in FIG. 1, the internal conductor front side extended portion 41*b* and the inner insulating layer front side extended portion 43*a* of the coaxial cable 40 extend in directions different from each other from the portion near the front end of the outer insulating layer 44 toward the electrode pads 24 to be soldered.

The distal ends (front ends) of the internal conductor front side extended portion 41*b* and the external conductor aggregate-wire portion 42*b* of the coaxial cable 40 are disposed apart from each other in an extending direction of the device main body rear surface 23 (a direction perpendicular to the front-rear direction of the imaging unit 10). Further, solder 11*a* that has soldered the distal end (front end) of the internal conductor front side extended portion 41*b* to an electrode pad 24 of the imaging device 20 is provided separately from solder 11*b* that has soldered the distal end (front end) of the external conductor aggregate-wire portion 42*b* to an electrode pad 24 of the imaging device 20

The internal conductor front side extended portion 41*b* and the external conductor aggregate-wire portion 42*b* of the coaxial cable 40 are maintained in a state in which they are not short-circuited.

In terms of forming the imaging module 100 in which the imaging unit 10 is housed in the protective tube 110 (see FIG. 3) to be as narrow as possible, it is advantageous to make a cross-sectional dimension perpendicular to the front-rear direction of the imaging head 10H of the imaging unit 10 as small as possible.

The distance between the electrode pads 24 adjacent to each other on the device main body rear surface 23 of the imaging device 20 may be less than 1 mm in some cases.

Since the external conductor aggregate-wire portion 42*b* is one in which the front side extended portions of the plurality of external conductor element wires 42*a* are aggregated, spreading of the front side extended portions of the external conductor element wires 42*a* between the device main body rear surface 23 of the imaging device 20 and the front end of the outer insulating layer 44 can be reduced to be small compared to a configuration in which the front side extended portions of the plurality of external conductor element wires 42*a* are soldered to the electrode pads 24 of the imaging device 20 without forming an aggregate-wire.

Employment of the external conductor aggregate-wire portion 42*b* effectively contributes to avoiding contact and short-circuiting of the front side extended portions of the external conductor element wires 42*a* with the cable conductors such as the internal conductor front side extended portion 41*b* and the external conductor aggregate-wire portion 42*b* (an external conductor aggregate-wire portion 42*b* of the other coaxial cable 40) which are positioned around the external conductor aggregate-wire portion 42*b* or with solder with which these cable conductors have been fixed to the electrode pads 24 of the imaging device 20.

When the distance between the electrode pads 24 adjacent to each other on the device main body rear surface 23 of the imaging device 20 is small (for example, 0.2 mm or more and less than 1 mm), employment of the external conductor aggregate-wire portion 42*b* is advantageous in avoiding contact and short-circuiting of the front side extended portions of the external conductor element wires 42*a* with the cable conductors positioned around the external conductor aggregate-wire portion 42*b* or with solder with which the cable conductors have been fixed to the electrode pads 24 of the imaging device 20.

Compared to an untwisted aggregate-wire, the external conductor aggregate-wire portion of the twisted aggregate-wire has excellent stability in cross-sectional dimension (cross-sectional outer dimension) perpendicular to an extending direction thereof with respect to repeated bending or the like, and thus spreading of the front side extended portions of the external conductor element wires 42*a* does not easily occur. Therefore, compared to an untwisted aggregate-wire, the external conductor aggregate-wire portion 42*b* of the twisted aggregate-wire is advantageous in stably maintaining a state in which short-circuiting with the cable conductors around the external conductor aggregate-wire portion 42*b* or solder at which the cable conductors have been fixed to the electrode pads 24 of the imaging device 20 is avoided over a long period of time.

In the external conductor aggregate-wire portion 42*b* of the twisted aggregate-wire, an outer diameter of the external conductor aggregate-wire portion 42*b* itself can be reduced to be small compared to that of untwisted aggregate-wires. The external conductor aggregate-wire portion 42*b* of the twisted aggregate-wire is advantageous in avoiding short-circuiting with cable conductors around the external conductor aggregate-wire portion 42*b* or with solder at which the cable conductors have been fixed to the electrode pads 24 of the imaging device 20.

In the internal conductor front side extended portion 41*b* and the external conductor aggregate-wire portion 42*b* of the coaxial cable 40 of the imaging unit 10 of FIGS. 1 and 2, there is solder which has entered between the element wires constituting each of them. The internal conductor front side extended portion 41*b* and the external conductor aggregate-wire portion 42*b* are configured such that the element wires constituting them are integrated by solder being between the element wires.

The internal conductor front side extended portion 41*b* and the external conductor aggregate-wire portion 42*b* integrated by solder entered between the element wires have excellent stability in cross-sectional dimension (cross-sectional outer dimension) perpendicular to an extending direction thereof compared to a configuration in which solder is not entered between element wires. The internal conductor front side extended portion 41*b* and the external conductor aggregate-wire portion 42*b* integrated by solder entered between the element wires can stably maintain a state in which short-circuiting with cable conductors therearound is avoided over a long period of time compared to a configuration in which solder is not entered between element wires.

Employment of the external conductor aggregate-wire portion 42*b* of the twisted aggregate-wire and the integration of the element wires 42*a* constituting the external conductor aggregate-wire portion 42*b* with solder effectively contribute to stabilization of the cross-sectional outer dimension of the external conductor aggregate-wire portion 42*b*.

Further, for the external conductor aggregate-wire portion 42*b* of the untwisted aggregate-wires as well, integration of the element wires 42*a* constituting the external conductor aggregate-wire portion 42*b* with solder effectively contributes to stabilization of a cross-sectional outer dimension thereof.

The configuration in which a distal end of the external conductor aggregate-wire portion 42b formed on the coaxial cable 40 is soldered to the electrode pad 24 of the imaging device 20 is advantageous in restricting a soldering range of the front side extended portions of the external conductor element wires 42a with respect to the electrode pad 24 of the imaging device 20 to be small. The fact that the soldering range of the front side extended portions of the external conductor element wires 42a with respect to the electrode pad 24 of the imaging device 20 can be restricted to be small effectively contributes to eliminating or reducing protrusion of the solder 11b, in which the distal end of the external conductor aggregate-wire portion 42b is soldered to the electrode pad 24 of the imaging device 20, from the electrode pad 24 to be small.

Therefore, the configuration in which the distal end of the external conductor aggregate-wire portion 42b formed on the coaxial cable 40 is soldered to the electrode pad 24 of the imaging device 20 is advantageous in reducing a size of the electrode pad 24, reducing a separation distance between the electrode pads 24 of the imaging device 20, and reducing a cross-sectional dimension perpendicular to the front-rear direction of the imaging device 20.

The internal conductor front side extended portion 41b and the external conductor aggregate-wire portion 42b of the coaxial cable 40 shown in FIGS. 1 and 2 are soldered in a state in which the distal ends (front ends) are respectively butt-jointed to the electrode pads 24 of the imaging device 20. The distal end portions (front end portions) of the internal conductor front side extended portion 41b and the external conductor aggregate-wire portion 42b are oriented substantially perpendicular to surfaces of the electrode pads 24 of the imaging device 20.

The configuration in which the distal ends of the internal conductor front side extended portion 41b and the external conductor aggregate-wire portion 42b are soldered in a state in which they are respectively butt-jointed to the electrode pads 24 of the imaging device 20 is advantageous in reducing an extension range of the solder on the surface of the electrode pads 24, in which the distal end portions of the internal conductor front side extended portion 41b and the external conductor aggregate-wire portion 42b are respectively soldered to the electrode pads 24, to be small, and effectively contributes to eliminating or reducing protrusion of the solder from an outer periphery of the electrode pads 24 to an outer side to be small.

The configuration in which the distal ends of the internal conductor front side extended portion 41b and the external conductor aggregate-wire portion 42b are soldered in a state in which they are respectively butt-jointed to the electrode pads 24 of the imaging device 20 is advantageous in reducing a size of the electrode pad 24, reducing a separation distance between the electrode pads 24 of the imaging device 20, and reducing a cross-sectional dimension perpendicular to the front-rear direction of the imaging device 20.

(Imaging Module)

As shown in FIG. 3, the protective tube 110 of the imaging module 100 may be, for example, a flexible tube formed of a synthetic resin such as a silicone resin.

Polyurethane, polyethylene, polytetrafluoroethylene (PTFE), or the like can be employed as a material for forming the protective tube 110 in addition to a silicone resin.

As shown in FIG. 3, in the imaging module 100, the imaging head 10H of the imaging unit 10 is housed in one end portion (front end portion) in a longitudinal direction of the protective tube 110. The imaging head 10H is provided in a front end portion of the protective tube 110 in such an orientation that the imaging device 20 is positioned on a rear end side of the lens unit 30 opposite to the front end portion of the protective tube 110.

The coaxial cable 40 extends inside the protective tube 110 from the imaging device 20 toward a rear end of the protective tube 110. The coaxial cable 40 includes a rear end portion extended from the rear end of the protective tube 110 to the outside of the protective tube 110. A portion of the coaxial cable 40 other than the rear end portion extended from the rear end of the protective tube 110 is entirely housed in the protective tube 110.

Rear end portions of the internal conductor 41 and the external conductor 42 of the coaxial cable 40 (a portion positioned at the rear end portion of the coaxial cable 40) are electrically connected to external devices such as a power supply device, a controller, a signal processing device, or an image processing device, for example.

For example, the internal conductor 41 may be used as a signal line for supplying a signal to the imaging device 20, and the external conductor 42 may be used as a power supply line for supplying power to the imaging device 20.

The imaging device 20 receives light incident on the lens unit 30 from a front side thereof through the lens in the lens housing 31 and captures an image.

(Manufacturing Method of Imaging Unit)

Here, an example of an assembly method of the imaging unit 10 (a manufacturing method of an imaging unit) will be described.

The imaging unit 10 can be manufactured by performing a lens unit fixing step of fixing the lens unit 30 to the front surface 22 of the imaging device 20 and a cable connecting step of electrically connecting the coaxial cable 40 to the imaging device 20.

The lens unit fixing step may be either before or after the cable connecting step, and may be performed in parallel with the cable connecting step.

In the cable connecting step, the coaxial cable 40 is prepared, and the outer insulating layer 44 at a distal end portion of the coaxial cable 40 is removed to expose the external conductor 42 (to secure the front side extended portions of the external conductor element wires 42a) and form the front side protruding portion of the inner coated wire 45. Next, a plurality of front side extended portions of the external conductor element wires 42a are aggregated to form the external conductor aggregate-wire portion 42b.

When the external conductor aggregate-wire portion 42b of the twisted aggregate-wire is formed in the cable connecting step, the plurality of front side extended portions of the external conductor element wires 42a are aggregated and twisted into a single linear shape.

When the external conductor aggregate-wire portion 42b of the untwisted aggregate-wire is formed, a plurality of front side extended portions of the external conductor element wires 42a are aggregated in a state in which they are substantially parallel to each other without being twisted to form a single linear shape.

Regarding the front side protruding portion of the inner coated wire 45, after the front side extended portions of the surrounding external conductor element wires 42a are spaced apart from the inner insulating layer front side extended portion 43a, the inner insulating layer 43 at the front end portion thereof is removed so that the front side extended portion 41b of the internal conductor 41 is secured.

After the external conductor element wires 42a are exposed by removing the outer insulating layer 44 at the distal end portion of the coaxial cable 40, in order to facilitate formation of the external conductor aggregate-wire portion 42b by twisting the front side extended portions of the external conductor element wires 42a together, before the external conductor aggregate-wire portion 42b is formed, if necessary, the front side extended portion may be cut off for a portion of the plurality of external conductor element wires 42a so that the number of the external conductor element wires 42a used for the formation of the external conductor aggregate-wire portion 42b is adjusted.

When the internal conductor front side extended portion 41b and the external conductor aggregate-wire portion 42b are secured in the coaxial cable 40, a preliminary soldering processing in which the internal conductor front side extended portion 41b and the external conductor aggregate-wire portion 42b are impregnated with heat-melted solder and then cooled and solidified is performed. Next, the distal ends of the internal conductor front side extended portion 41b and the external conductor aggregate-wire portion 42b are respectively soldered to the electrode pads 24 of the imaging device 20.

Soldering of the respective distal ends of the internal conductor front side extended portion 41b and the external conductor aggregate-wire portion 42b to the electrode pads 24 of the imaging device 20 is performed by heat-melting solder (for example, solder bump) provided on the electrode pads 24 in advance or solder separately provided in the portion near the electrode pads 24 and thereafter by cooling and solidifying the solder.

When soldering of the respective distal ends of the internal conductor front side extended portion 41b and the external conductor aggregate-wire portion 42b to the electrode pads 24 of the imaging device 20 is completed, the cable connecting step for electrically connecting the coaxial cable 40 to the imaging device 20 is completed.

In the assembly of the imaging unit 10 of FIGS. 1 and 2, the cable connecting step with respect to the imaging device 20 is completed when the respective distal ends of the internal conductor front side extended portion 41b and the external conductor aggregate-wire portion 42b of the two coaxial cables 40 are soldered to the electrode pads 24 of the imaging device 20.

Further, in the cable connecting step, with the preliminary soldering processing omitted, the plurality of element wires of the respective internal conductor front side extended portion 41b and the external conductor aggregate-wire portion 42b can be brought into an integrated state by causing the internal conductor front side extended portion 41b and the external conductor aggregate-wire portion 42b to be impregnated with solder that solders the distal ends thereof to the electrode pads 24 of the imaging device 20 in a heat-melted state and then cooled and solidified.

Since the external conductor aggregate-wire portion 42b formed in the coaxial cable 40 is formed by aggregating the plurality of front side extended portions of the external conductor element wires 42a, a soldering range of the imaging device 20 with respect to the electrode pad 24 can be restricted to be small compared to the case in which the aggregate-wire portion of the external conductor element wires 42a is not formed. Therefore, forming the external conductor aggregate-wire portion 42b to be soldered to the electrode pad 24 of the imaging device 20 is advantageous in terms of improving work efficiency and workability in soldering of the front extended portions of the external conductor element wires 42a to the electrode pads 24 of the imaging device 20.

Further, forming the external conductor aggregate-wire portion 42b to be soldered to the electrode pad 24 of the imaging device 20 is advantageous in soldering the front side extended portions of the external conductor element wires 42a to the electrode pad 24 to be soldered without being in contact with an electrode pad 24 around the electrode pad 24 to be soldered, a surrounding cable conductor therearound, or the like.

In the external conductor aggregate-wire portion 42b which is a twisted aggregate-wire, scattering (spreading) of the front side extended portions of the external conductor element wires 42a does not easily occur compared to an untwisted aggregate-wire.

Also, in the external conductor aggregate-wire portion 42b on which the preliminary soldering processing has been performed, scattering (spreading) of the front side extended portions of the external conductor element wires 42a does not easily occur compared to a case in which the preliminary soldering processing has not been performed.

Employing the twisted aggregated-wire for the external conductor aggregate-wire portion 42b and performing the preliminary soldering processing on the external conductor aggregate-wire portion 42b facilitate soldering of the external conductor aggregate-wire portion 42b to the electrode pad 24 to be soldered without being in contact with an electrode pad 24 around the electrode pad 24 to be soldered, a surrounding cable conductor thereof, or the like.

In the imaging unit 10 shown in FIG. 1, the imaging head 10H has a strength that cannot be easily subjected to bending deformation and constitutes a part of a rigid portion of the imaging unit 10.

Also, in the imaging unit 10 shown in FIG. 1, the inner coated wire 45 (including the internal conductor front side extended portion 41b) and the external conductor aggregate-wire portion 42b of the coaxial cable 40 which are protruding from the front end of the outer insulating layer 44 cannot be easily bent and constitute a part of the rigid portion of the imaging unit 10.

In the imaging unit 10 shown in FIG. 1, a range from the front end of the lens unit 30 to the front end of the outer insulating layer 44 of the coaxial cable 40 constitutes a rigid portion 10C which does not easily bend.

In the imaging unit 10 shown in FIG. 1, the respective front ends of the internal conductor front side extended portion 41b and the external conductor aggregate-wire portion 42b are fixed to the imaging device 20, and a separation distance between the front end of the internal conductor front side extended portion 41b and the front end of the external conductor aggregate-wire portion 42b is fixed.

In the imaging unit 10 shown in FIG. 1, the inner coated wire 45 (including the internal conductor front side extended portion 41b) and the external conductor aggregate-wire portion 42b which are extending from the front end of the outer insulating layer 44 of the coaxial cable 40 and the imaging device 20 form a structure 10T in a triangular frame shape (hereinafter also referred to as a triangular frame portion).

The triangular frame portion 10T constitutes a part of the rigid portion 10C of the imaging unit 10.

The rigid portion 10C of the imaging unit 10 in FIG. 1 is constituted by the imaging head 10H and the triangular frame portion 10T on the rear side thereof.

The imaging device 20 of the imaging unit 10 can change an orientation of the imaging surface with respect to a front end of the cable main body 46 by rotation (swinging) around the front end of the coaxial cable main body 46 of the rigid portion 10C.

Extended lengths of the imaging unit 10 shown in FIG. 1 from the respective distal ends at the coaxial cable main body 46 of the internal conductor 41 and the external conductor aggregate-wire portion 42b (the front end of the outer insulating layer 44) to the electrode pads 24 of the imaging device 20 are the same as each other.

An external force acting on the rigid portion 10C of the imaging unit 10 in a direction to change an orientation thereof with respect to the front end of the coaxial cable main body 46 (a rotational direction with respect to the front end of the cable main body 46) will also be hereinafter referred to as a swinging force. The extended length portions from the respective front ends at the coaxial cable main body 46 of the internal conductor 41 and the external conductor aggregate-wire portion 42b (the front ends of the outer insulating layer 44) to the electrode pads 24 of the imaging device 20 do not easily deform due to a rigidity of the internal conductor 41 and the external conductor aggregate-wire portion 42b themselves even when an orientation of the imaging head 10H with respect to the front end of the coaxial cable main body 46 is changed by an external force (swinging force).

From a structural perspective, the triangular frame portion 10T can disperse a swinging force acting on the imaging head 10H over an entire triangular frame portion 10T. Therefore, in the imaging unit 10, it is possible to prevent the swinging force acting on the imaging head 10H from locally acting on a part of the inner coated wire 45 and the external conductor aggregate-wire portion 42b. Also, from this perspective, in the imaging unit 10, deformation of the imaging unit 10 relative to the inner coated wire 45 and external conductor aggregate-wire portion 42b does not easily occur.

Further, the configuration of the internal conductor 41 and the external conductor aggregate-wire portion 42b being a twisted aggregate-wire in which a plurality of element wires are twisted together and the configuration thereof in which the plurality of element wires are integrated by solder increase a rigidity of the inner coated wire 45 and the external conductor aggregate-wire portion 42b.

Even when the orientation of the imaging head 10H with respect to the front end of the coaxial cable main body 46 is changed by an external force (swinging force), deformation of the inner coated wire 45 and the external conductor aggregate-wire portion 42b does not easily occur and the triangular frame portion 10T of the imaging unit 10 displaces with respect to the front end of the cable main body 46 while maintaining the triangular frame shape.

Therefore, even when the orientation of the rigid portion 10C with respect to the front end of the coaxial cable main body 46 changes due to swinging, a state in which the imaging surface of the imaging device 20 of the imaging unit 10 is perpendicular to a radius of rotation of the rigid portion 10C with respect to the front end of the coaxial cable main body 46 due to swinging is maintained.

In the imaging unit 10, the imaging device 20 can be moved on a circumference around the front end of the coaxial cable main body 46 by changing the orientation of the rigid portion 10C with respect to the front end of the coaxial cable main body 46 by swinging. Therefore, in the imaging unit 10, adjustment of the orientation of the imaging device 20 can be performed with high accuracy by swinging operation of the rigid portion 10C with respect to the front end of the coaxial cable main body 46.

Further, as long as it has a configuration in which the imaging device 20 is moved on the circumference around the front end of the coaxial cable main body 46 by swinging of the rigid portion 10C with respect to the front end of the coaxial cable main body 46, an image being captured by the imaging device 20 during the swinging operation of the rigid portion 10C can be stabilized.

As shown in FIG. 1, the imaging unit 10 has a configuration in which the respective front ends of the internal conductor front side extended portion 41b and the external conductor aggregate-wire portion 42b of the front end portion of the coaxial cable 40 are directly soldered to the electrode pads 24 of the imaging device 20 without interposing a coaxial cable wiring substrate therebetween.

Therefore, a rigid portion length L can be reduced in the imaging unit 10 as compared with imaging units of a conventional configuration in which a coaxial cable wiring substrate is used.

With respect to the rigid portion 10C of the imaging unit 10 shown in FIGS. 1 and 2, a separation distance from the front end of the coaxial cable main body 46 in the front-rear direction (coinciding with the front-rear direction of the imaging device 20) to the front end of the lens unit 30 will also be referred to as a swinging radius hereinafter. In the imaging unit 10 shown in FIGS. 1 and 2, the swinging radius of the rigid portion 10C coincides with the rigid portion length L.

Reduction of the rigid portion length L of the imaging unit 10 can cause reduction of the swinging radius of the rigid portion 10C around the front end of the coaxial cable main body 46. As a result, the swinging radius (a distance from the front end of the cable main body 46 to a front end of the protective tube 110) of the front end portion (an end portion on a side at which a front end wall portion 112 is positioned) of the imaging module 100 (see FIG. 3) around the front end of the coaxial cable main body 46 can be reduced.

Reduction of the rigid portion length L of the imaging unit 10 can be advantageous for increasing the swinging range of the rigid portion 10C around the front end of the coaxial cable main body 46 (a range of swinging angle of the rigid portion 10C with respect to a central axis of the front end of the coaxial cable main body 46. Movable range) in a narrow conduit or the like.

Therefore, reduction of the rigid portion length L of the imaging unit 10 effectively contributes to, for example, facilitating an operation of inserting the front end portion of the imaging module 100 into a bent portion of a conduit and passing it therethrough, allowing the front end portion of the imaging module 100 to pass through a narrower bent portion of a conduit, or the like.

The imaging module 100 shown in FIG. 3 can also employ, for example, a configuration in which a swinging mechanism is housed in a swinging mechanism lumen formed to extend in an extending direction of the protective tube 110 and the front end portion of the imaging module 100 is rotated around the front end of the coaxial cable main body 46 by the swinging mechanism to change (swing) the orientation of the imaging module 100 with respect to the front end of the cable main body 46. In the imaging module 100 (imaging module with swinging mechanism) in which the swinging mechanism is housed in the swinging mechanism lumen of the protective tube 110, reduction of the rigid portion length L of the imaging unit 10 can cause the swinging radius of the front end portion of the imaging module around the front end of the coaxial cable main body 46 to be reduced.

Next, an imaging unit according to one or more embodiments of the invention will be described.

Figure 4:
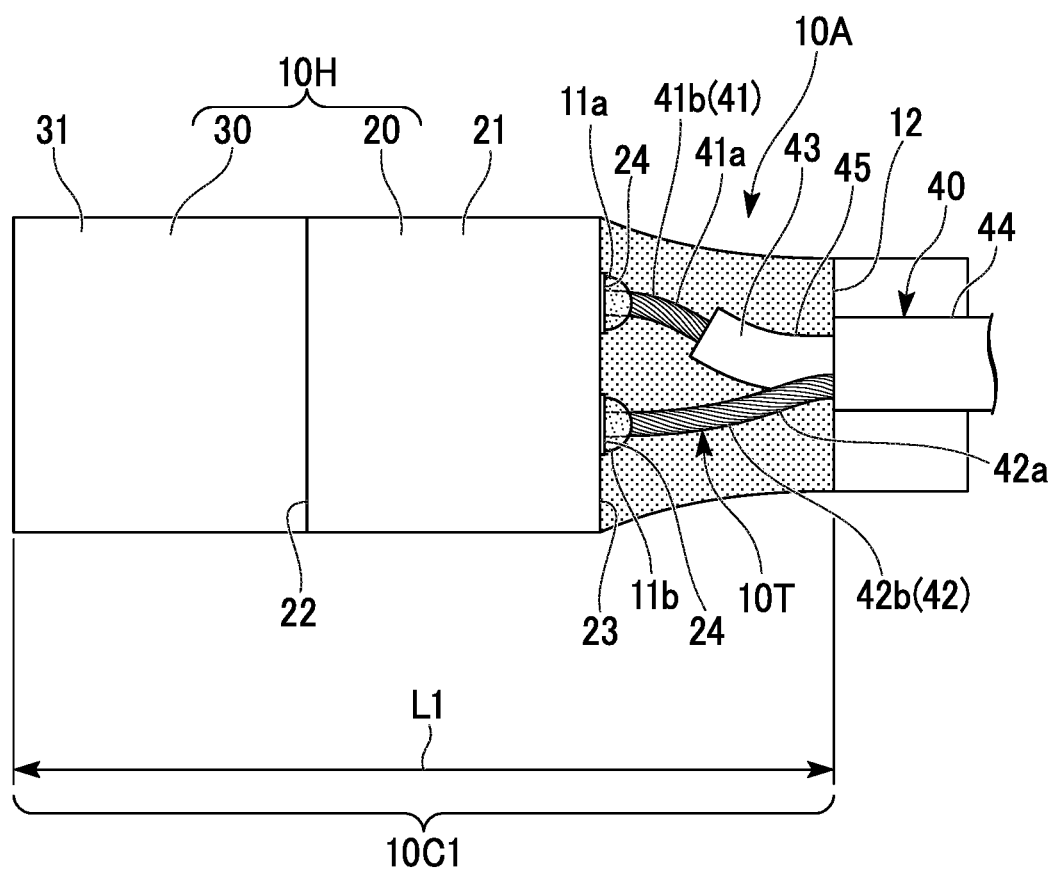
FIG. 4 is a front view showing a structure in the portion near an imaging head of an imaging unit according to one or more embodiments of the invention.

FIG. 4 shows an imaging unit 10A according to one or more embodiments.

As shown in FIG. 4, the imaging unit 10A according to one or more embodiments is configured such that a protective resin portion 12 in which an inner coated wire 45 and an external conductor aggregate-wire portion 42b constituting a triangular frame portion 10T thereof are implanted in and covered is provided in the imaging unit 10 shown in FIGS. 1 and 2.

The protective resin portion 12 is formed by curing a liquid resin material supplied between an imaging device 20 and a front end of a cable main body 46 of a coaxial cable 40 using, for example, an injector.

Further, the protective resin portion 12 may be formed, for example, by curing a liquid resin material supplied into a mold provided to surround the inner coated wire 45 and external conductor aggregate-wire portion 42b constituting the triangular frame portion 10T and then used with the mold removed after the formation.

Also, the protective resin portion 12 is adhered and fixed also to the imaging device 20 by an adhesive force of the protective resin portion 12 itself (an adhesive force developed by the curing of the liquid resin material for forming the protective resin portion 12).

Both a configuration in which the protective resin portion 12 is adhered and fixed to any one or both of the inner coated wire 45 and the external conductor aggregate-wire portion 42b and a configuration in which the protective resin portion 12 is adhered and fixed to neither the inner coated wire 45 nor the external conductor aggregate-wire portion 42b can be employed.

The protective resin portion 12 is formed in contact with a rear surface 23 of the imaging device 20. The inner coated wire 45 and the external conductor aggregate-wire portion 42b of all the coaxial cables 40 connected to the imaging device 20 (two in FIGS. 1 and 2) are implanted in and coated with the protective resin portion 12.

In FIG. 4, the protective resin portion 12 is formed only in a front side region from a front end of the coaxial cable main body 46, and is not formed on a rear side of the front side region from the front end of the coaxial cable main body 46 (a side opposite to the imaging device 20).

The protective resin portion 12 is formed of a resin excellent in electrical insulation, for example, such as an epoxy resin, an acrylic resin, or a phenolic resin.

For the protective resin portion 12, a material capable of securing a sufficiently high dielectric breakdown voltage with respect to a potential difference generated between the cable conductors positioned therein is employed.

The protective resin portion 12 serves to inhibit bending of the inner coated wire 45 and the external conductor aggregate-wire portion 42b present therein. The protective resin portion 12 contributes to maintaining a shape of the triangular frame portion 10T.

The protective resin portion 12 constitutes a portion of a rigid portion 10C1 of the imaging unit 10A in FIG. 4.

The protective resin portion 12 of the imaging unit 10A in FIG. 4 prevents deformation of the inner coated wire 45 and the external conductor aggregate-wire portion 42b due to swinging of an imaging head 10H with respect to the front end of the coaxial cable main body 46 or the like, and the consequent contacts and short-circuiting between the cable conductors.

The protective resin portion 12 serves to stably maintain the shape of the triangular frame portion 10T.

The imaging unit 10A in FIG. 4 includes the rigid portion 10C1 including the imaging head 10H, the inner coated wire 45 and the external conductor aggregate-wire portion 42b, and a protective resin portion 12.

In the imaging unit 10A in FIG. 4, the rigid portion 10C1 can be swung, which is rotation around the front end of the coaxial cable main body 46 with respect to the front end of the coaxial cable main body 46.

The rigid portion 10C1 of the imaging unit 10A of FIG. 4 is swung with a swinging radius which is a separation distance from the front end of the coaxial cable main body 46 to a front end of a lens unit 30.

The swinging radius of the rigid portion 10C1 of the imaging unit 10A in FIG. 4 coincides with a rigid portion length L1 which is a dimension in a front-rear direction of the rigid portion 10C1 (coincides with the front-rear direction of the imaging device).

As shown in FIG. 4, the front end portion of the coaxial cable main body 46 is not implanted in the protective resin portion 12. The protective resin portion 12 is formed to avoid an outer insulating layer 44 of the coaxial cable 40 from being implanted thereinto. In the imaging unit 10A of FIG. 4, the protective resin portion 12 does not obstruct rotation (swinging) of the rigid portion 10C1 around the front end of the coaxial cable main body 46.

Next, an imaging unit according to one or more embodiments of the invention will be described.

Figure 5:
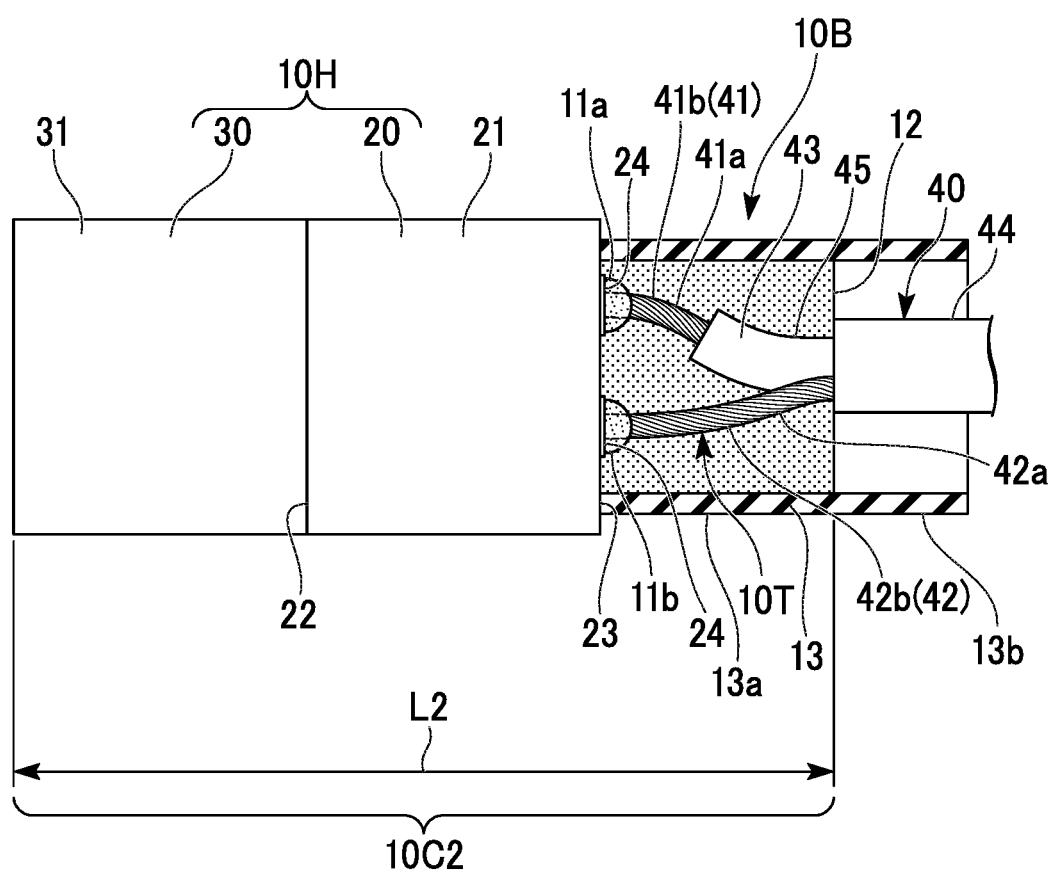
FIG. 5 is a front view showing a structure in the portion near an imaging head of an imaging unit according to one or more embodiments of the invention.

FIG. 5 shows an imaging unit 10B according to one or more embodiments.

As shown in FIG. 5, the imaging unit 10B according to one or more embodiments is configured such that a resin sleeve 13 in which an inner coated wire 45 and an external conductor aggregate-wire portion 42b constituting a triangular frame portion 10T thereof are housed is provided in the imaging unit 10A of the previously-described embodiments, and a protective resin portion 12 in which the inner coated wire 45 and the external conductor aggregate-wire portion 42b are implanted in and covered is provided in the resin sleeve 13.

Further, in FIG. 5, the same references are given to components the same as those in the imaging unit 10A of the previously-described embodiments, and description thereof will be omitted or simplified.

The resin sleeve 13 is a tubular member formed of a resin and is excellent in flexibility.

The resin sleeve 13 can be used as an injection mold in which a curable liquid resin material forming the protective resin portion 12 is injected when the protective resin portion 12 is formed.

The resin sleeve 13 is formed in such a size that its entirety is positioned within a projection range in a front-rear direction of a rear surface 23 of an imaging device 20 in a state in which a central axis thereof is parallel to the front-rear direction of the imaging device 20. A front end surface (an end surface on the imaging device 20 side) of one end in an axial direction of the resin sleeve 13 can be in contact with a rear surface 23 of the imaging device 20 as a whole.

The protective resin portion 12 is formed by curing a liquid resin material injected into the resin sleeve 13.

The resin sleeve 13 is adhered and fixed to the protective resin portion 12 by an adhesive force developed by curing of the liquid resin material for forming the protective resin portion 12. The resin sleeve 13 is supported by the triangular frame portion 10T via the protective resin portion 12.

Also, the protective resin portion 12 is adhered and fixed also to the imaging device 20 by the adhesive force of the protective resin portion 12 itself (an adhesive force developed by curing of the liquid resin material for forming the protective resin portion 12).

Both a configuration in which the protective resin portion 12 is adhered and fixed to any one or both of the inner coated wire 45 and the external conductor aggregate-wire portion 42b and a configuration in which the protective resin portion 12 is adhered and fixed to neither the inner coated wire 45 nor the external conductor aggregate-wire portion 42b can be employed.

The resin sleeve 13 houses the inner coated wire 45 and external conductor aggregate-wire portion 42b of all the coaxial cables 40 connected to the imaging device 20 inside thereof.

The protective resin portion 12 is filled in the entire region on a front side from a front end of the coaxial cable main body 46 inside the resin sleeve 13. The protective resin portion 12 is formed in contact with the rear surface 23 of the imaging device 20. The inner coated wire 45 and the external conductor aggregate-wire portion 42b of all the coaxial cables 40 connected to the imaging device 20 (two in FIGS. 1 and 2) are implanted in and covered with the protective resin portion 12.

In FIG. 5, the protective resin portion 12 is formed only in a front side region from the front end of the coaxial cable main body 46 inside the resin sleeve 13, and is not formed on a rear side of the front side region from the front end of the coaxial cable main body 46 (a side opposite to the imaging device 20).

The protective resin portion 12 serves to inhibit bending of the inner coated wire 45 and the external conductor aggregate-wire portion 42b present therein. The protective resin portion 12 contributes to maintaining a shape of the triangular frame portion 10T.

The protective resin portion 12 constitutes a portion of a rigid portion 10C2 of the imaging unit 10B in FIG. 5.

The protective resin portion 12 of the imaging unit 10B in FIG. 5 prevents deformation of the inner coated wire 45 and the external conductor aggregate-wire portion 42b due to swinging of an imaging head 10H with respect to the front end of the coaxial cable main body 46 or the like, and the consequent contacts and short-circuiting between the cable conductors.

The protective resin portion 12 serves to stably maintain the shape of the triangular frame portion 10T.

The imaging unit 10B in FIG. 5 includes the rigid portion 10C2 constituted by the imaging head 10H, the inner coated wire 45 and the external conductor aggregate-wire portion 42b, the protective resin portion 12, and a portion of the resin sleeve 13 in which the protective resin portion 12 is housed (protective resin housing portion).

In the imaging unit 10B in FIG. 5, the rigid portion 10C2 can be swung, which is rotation around the front end of the coaxial cable main body 46 with respect to the front end of the coaxial cable main body 46.

The rigid portion 10C2 of the imaging unit 10B of FIG. 5 is swung with a swinging radius which is a separation distance from the front end of the coaxial cable main body 46 to a front end of a lens unit 30.

The swinging radius of the rigid portion 10C2 of the imaging unit 10B in FIG. 5 coincides with a rigid portion length L2 which is a dimension in a front-rear direction of the rigid portion 10C2 (coincides with the front-rear direction of the imaging device).

As shown in FIG. 5, the front end portion of the coaxial cable main body 46 is not implanted in the protective resin portion 12. The protective resin portion 12 is formed to avoid an outer insulating layer 44 of the coaxial cable 40 from being implanted thereinto. In the imaging unit 10B of FIG. 5, the protective resin portion 12 does not obstruct rotation (swinging) of the rigid portion 10C2 around the front end of the coaxial cable main body 46.

The resin sleeve 13 of the imaging unit 10B of FIG. 5 includes not only the inner coated wire 45, external conductor aggregate-wire portion 42b, and the protective resin portion 12, but also a front end portion of the cable main body 46 which is the front end of the coaxial cable main body 46 and a rear side portion thereof.

The resin sleeve 13 includes a portion 13a in which the protective resin portion 12 is housed (a protective resin housing portion), and a portion 13b extending from the protective resin housing portion 13a to the rear side and in which the front end portion of the coaxial cable main body 46 is housed (hereinafter referred to as a cable main body housing portion).

The resin sleeve 13 is formed in a tubular shape extending at an inner diameter capable of housing the inner coated wire 45 and external conductor aggregate-wire portion 42b of all the coaxial cables 40 connected to the imaging device 20 (two in FIGS. 1 and 2). The inner diameter of the resin sleeve 13 is larger than an outer diameter of the cable main body 46 of the coaxial cable 40. There is a clearance between the front end portion of the coaxial cable main body 46 and the cable main body housing portion 13b of the resin sleeve 13 housing the front end portion of the coaxial cable main body 46.

The cable main body housing portion 13b of the resin sleeve 13 can be brought into contact with the front end portion of the cable main body 46 by swinging with respect to the front end of the coaxial cable main body 46 of the rigid portion 10C2.

Since the protective resin housing portion 13a of the resin sleeve 13 is integrated with the protective resin portion 12 by adhesion with the protective resin portion 12, bending does not easily occur, whereas the cable main body housing portion 13b of the resin sleeve 13 is not adhered to the protective resin portion 12 and is flexible and excellent in flexibility. The cable main body housing portion 13b of the resin sleeve 13 is easily deformed when it is pressed against the front end portion of the cable main body 46 by swinging of the rigid portion 10C2 with respect to a central axis of the front end of the coaxial cable main body 46. Even in a state in which the cable main body housing portion 13b of the resin sleeve 13 is in contact with the front end portion of the cable main body 46, the rigid portion 10C2 can swing with respect to the front end of the coaxial cable main body 46 while deforming the cable main body housing portion 13b of the resin sleeve 13.

Next, an imaging unit according to one or more embodiments of the invention will be described with reference to FIG. 6.

Figure 6:
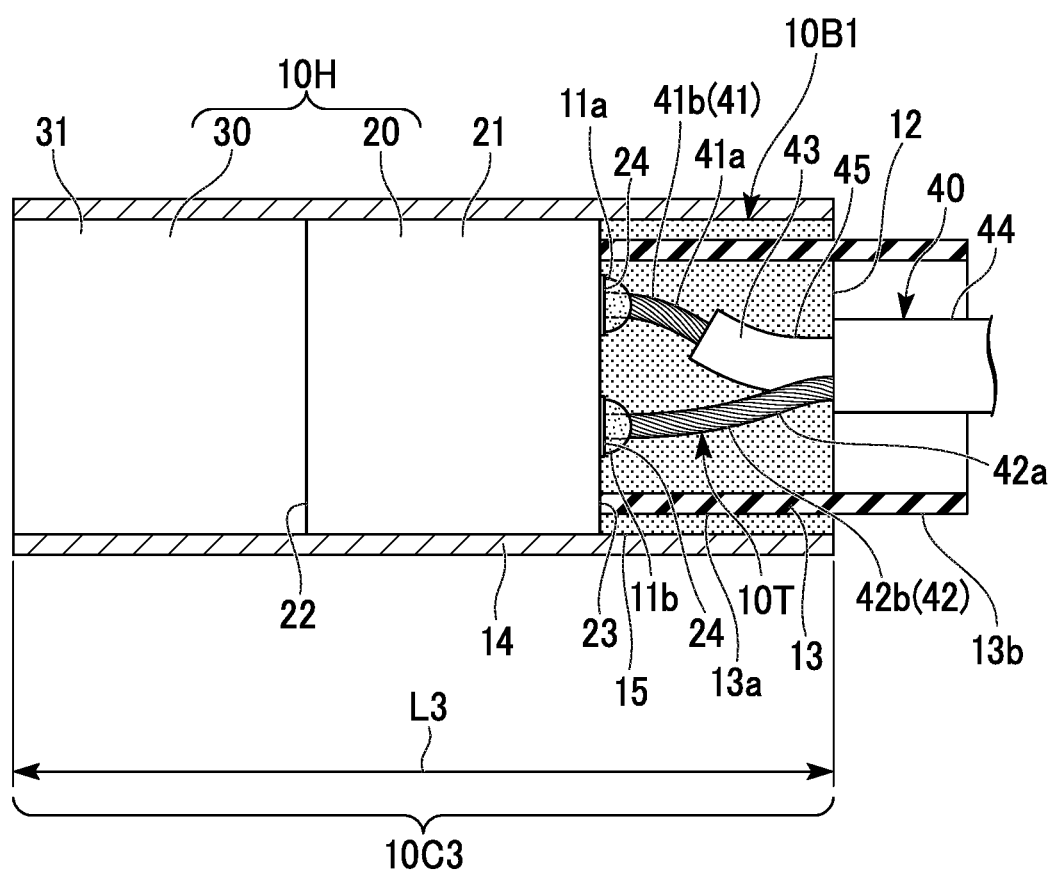
FIG. 6 is a front view showing a structure in the portion near an imaging head of an imaging unit according to one or more embodiments of the invention.

As shown in FIG. 6, in an imaging unit 10B1 according to one or more embodiments, an exterior sleeve 14 housing the rigid portion 10C2 in the imaging unit 10B of the previously-described embodiments is provided.

The exterior sleeve 14 may be a hard cylindrical member formed of, for example, a metal, a resin, or the like.

For the exterior sleeve 14, the exterior sleeve 14 in a cylindrical shape can be suitably employed.

A front end of the exterior sleeve 14 of the imaging unit 10B1 shown in FIG. 6 is aligned at a front end of a lens unit 30, and a rear end of the exterior sleeve 14 is aligned at a rear end of a protective resin housing portion 13a of a resin sleeve 13. The exterior sleeve 14 is fixed (adhered and fixed) to the protective resin housing portion 13a of the resin sleeve 13 by an adhesive force of an inter-sleeve resin 15 filled between an inner surface thereof and the resin sleeve 13.

The exterior sleeve 14 formed of a good conductor metal, for example, such as stainless steel can also be employed.

When the exterior sleeve 14 formed of a good conductor metal is used, one having electrical insulation properties is employed as the resin sleeve 13 of the imaging unit 10B1 shown in FIG. 6. Employment of the electrically insulating resin sleeve 13 is for securely preventing conduction and short-circuiting with the exterior sleeve 14 made of a good conductor metal in the unlikely event that when cable conductors such as an internal conductor front side extended portion 41b and an external conductor aggregate-wire portion 42b are exposed on a surface of a protective resin portion 12.

The imaging unit 10B1 in FIG. 6 includes a rigid portion 10C3 constituted by an imaging head 10H, an inner coated wire 45 and the external conductor aggregate-wire portion 42b, the protective resin portion 12, the protective resin housing portion 13a of the resin sleeve 13, the exterior sleeve 14, and the inter-sleeve resin 15.

A portion other than the protective resin housing portion 13a of the resin sleeve 13, the exterior sleeve 14, and the inter-sleeve resin 15 in the rigid portion 10C3 of the imaging unit 10B1 in FIG. 6 will also be referred to as a rigid portion core portion hereinafter. The rigid portion core portion is constituted by the imaging head 10H, the inner coated wire 45 and the external conductor aggregate-wire portion 42b, and the protective resin portion 12.

The exterior sleeve 14 is a rigid body that houses the entire rigid portion core portion inside thereof to protect the rigid portion core portion from an external force such as a bending force, and stably maintains a shape of the rigid portion core portion.

A dimension in an axial direction (a dimension in a front-rear direction) of the exterior sleeve 14 of the imaging unit 10B1 shown in FIG. 6 is the same as a dimension in the front-rear direction of the rigid portion core portion.

A rigid portion length L3, which is a dimension in the front-rear direction of the rigid portion 10C3 of the imaging unit 10B1 (a dimension in a direction coinciding with the front-rear direction of the imaging device 20) in FIG. 6, is the same as the dimension in the axial direction of the exterior sleeve 14.

The rigid portion length L3 of the rigid portion 10C3 of the imaging unit 10B1 of FIG. 6 can be reduced to be as small as the rigid portion length L2 of the rigid portion 10C2 of the imaging unit 10B of FIG. 5.

For example, in FIG. 3 of Patent Document 1, an endoscope having an insulating tube which houses a substrate extending toward a rear side from an imaging device, and a front end portion of an electric cable soldered to the substrate on a rear side of the imaging device, and having a configuration in which a tubular outer frame member housing the insulating tube is adhered and fixed to the insulating tube with a resin is disclosed. The inside of the insulating tube is filled with a resin. In the endoscope shown in FIG. 3 of Patent Document 1, the imaging device, a lens unit fixed to a front side of the imaging device, the outer frame member, and contents contained inside the outer frame member are integrated, and in order to swing the imaging device, a front end portion of a portion of the electric cable extending to a rear side from the insulating tube needs to be bent.

In the configuration of FIG. 3 of Patent Document 1, a portion in which the imaging device, the lens unit fixed to the front side of the imaging device, the outer frame member, and contents contained inside the outer frame member are integrated functions as a rigid portion.

In contrast, the rigid portion 10C3 of the imaging unit 10B1 in FIG. 6 does not include a substrate for electrically connecting the imaging device 20 to the coaxial cable 40. Therefore, in the imaging unit 10B1 of FIG. 6, a rigid portion length of the rigid portion 10C3 can be reduced to be small and a movable range due to swinging of the rigid portion can easily be extended compared to the imaging unit having a substrate for electrically connecting an imaging device to a coaxial cable as in the technology of Patent Document 1.

The imaging units 10A, 10B, and 10B1 of the previously-described embodiments can be housed in the protective tube 110 (FIG. 3) and used for assembling an imaging module.

The imaging unit according to the previously-described embodiments of the invention can be housed in the protective tube 110 (FIG. 3) and used for assembling an imaging module.

The imaging unit can also employ a configuration in which the exterior sleeve 14 is provided to the imaging unit 10A of the previously-described embodiments, that is, a configuration in which the resin sleeve 13 and the inter-sleeve resin 15 are omitted from the imaging unit 10B1 of the previously-described embodiments and the protective resin portion 12 formed to have a size that can be in direct contact with an inner surface of the exterior sleeve 14 is provided inside the exterior sleeve 14.

Further, the imaging unit can also employ a configuration in which the resin sleeve 13 and the inter-sleeve resin 15 are omitted from the imaging unit 10B1 of the previously-described embodiments and a resin layer for filling between the protective resin portion 12 and the exterior sleeve 14 is formed.

While embodiments of the invention have been described and shown above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

The internal conductor of the coaxial cable is not limited to a twisted wire, and may be an untwisted aggregate-wire in which a plurality of element wires are aggregated in a state of being substantially parallel to each other without being twisted together. For a front side extended portion of the internal conductor of the untwisted aggregate-wire, both the twisted aggregate-wire in which a plurality of element wires of the untwisted aggregate-wire are twisted and the untwisted aggregate-wire can be employed.

However, the twisted aggregate-wire is superior to the untwisted aggregate-wire in terms of securing stability and rigidity in cross-sectional outer dimension against repeated bending or the like.

For the internal conductor front side extended portion 41b and the external conductor aggregate-wire portion 42b, a configuration in which solder is not entered between element wires can also be employed.

However, a configuration in which the internal conductor front side extended portion 41b and the external conductor aggregate-wire portion 42b are integrated by solder entered between the element wires is superior to a configuration in which solder is not entered between the element wires in terms of stability in cross-sectional outer dimension and securing a rigidity.

What is claimed is:

1. An imaging unit comprising:
    a solid-state imager comprising:
        an imaging surface on a front surface of the solid-state imager; and
        electrode pads disposed separately from each other on a rear surface of the solid-state imager that is opposite to the front surface; and
    a coaxial cable electrically connected to the electrode pads on the rear surface of the solid-state imager, wherein
    the coaxial cable comprises:
        an inner coated wire comprising:
            an internal conductor that comprises a plurality of element wires; and
            an inner insulating layer that coats a surrounding circumference of the internal conductor;
        an external conductor comprising a plurality of element wires that surround the inner coated wire; and
        an outer insulating layer that coats the external conductor,
    an external conductor aggregate-wire portion, comprising a plurality of element-wires of the external conductor are aggregated from a front end of the outer insulating layer, and the inner coated wire extend in different directions, and
    an internal conductor front side extended portion, that extends from a front end of the inner insulating layer of the inner coated wire that extends from the front end of the outer insulating layer, and the external conductor aggregate-wire portion are connected to the electrode pads on the rear surface of the solid-state imager.

2. The imaging unit according to claim 1, wherein
    extended lengths of the internal conductor and the external conductor aggregate-wire portion, from the front end of the outer insulating layer to the electrode pads of the solid-state imager, are the same.

3. The imaging unit according to claim 1, further comprising:
    a protective resin portion disposed on a rear side of the solid-state imager, wherein
    the inner coated wire and the external conductor aggregate-wire portion are implanted within the protective resin portion, and
    the protective resin portion avoids the outer insulating layer.

4. The imaging unit according to claim 3, further comprising:
    a resin sleeve that houses the protective resin portion, wherein
    the protective resin portion is disposed in an entire region inside the resin sleeve between the solid-state imager and the front end of the outer insulating layer.

5. The imaging unit according to claim 1, wherein
    one or both of the internal conductor front side extended portion and the external conductor aggregate-wire portion are a twisted aggregate-wire that comprises a plurality of element wires that are twisted together.

6. The imaging unit according to claim 1, wherein
    one or both of the internal conductor front side extended portion and the external conductor aggregate-wire portion comprise a plurality of element wires that are integrated with solder.

* * * * *